(12) United States Patent
Knorr et al.

(10) Patent No.: US 9,052,256 B2
(45) Date of Patent: Jun. 9, 2015

(54) METHOD FOR PROCESSING AND EMBEDDING TISSUE

(71) Applicant: LEICA BIOSYSTEMS NUSSLOCH GMBH, Nussloch (DE)

(72) Inventors: Stella Knorr, Brighton (AU); Andrew Guy, Coburg (AU); Ralf Eckert, Schriesheim (DE); Fiona Tarbet, Box Hill (AU); Fernando Dias, Endeavor Hills (AU); Chris Ryan, East Brunswick (AU); Neil Sanut, Pakenham (AU)

(73) Assignee: Leica Biosystems Nussloch GmbH, Nubloch (DE)

( * ) Notice: Subject to any disclaimer, the term of this patent is extended or adjusted under 35 U.S.C. 154(b) by 0 days.

(21) Appl. No.: 14/204,580

(22) Filed: Mar. 11, 2014

(65) Prior Publication Data

US 2014/0273083 A1      Sep. 18, 2014

Related U.S. Application Data

(60) Provisional application No. 61/799,924, filed on Mar. 15, 2013.

(51) Int. Cl.
*A61B 10/00* (2006.01)
*G01N 1/36* (2006.01)
*B01L 3/00* (2006.01)

(52) U.S. Cl.
CPC . *G01N 1/36* (2013.01); *B01L 3/502* (2013.01); *B01L 3/50855* (2013.01); *B01L 2300/0609* (2013.01)

(58) Field of Classification Search
CPC .......... G01N 1/36; B01L 3/502; A61B 10/00
See application file for complete search history.

(56) References Cited

U.S. PATENT DOCUMENTS

| | | | |
|---|---|---|---|
| 4,735,794 A | 4/1988 | Parkinson | |
| 4,801,553 A * | 1/1989 | Owen et al. | 436/174 |
| 5,269,671 A * | 12/1993 | McCormick | 425/117 |
| 5,401,625 A | 3/1995 | Robinson | |
| 5,447,841 A | 9/1995 | Gray et al. | |
| 5,601,650 A | 2/1997 | Goldbecker et al. | |
| 5,665,398 A * | 9/1997 | McCormick | 425/117 |
| 5,695,942 A | 12/1997 | Farmilo et al. | |
| 5,817,032 A | 10/1998 | Williamson, IV et al. | |
| 5,895,628 A | 4/1999 | Heid et al. | |
| 5,965,454 A | 10/1999 | Farmilo et al. | |
| 5,968,436 A | 10/1999 | Takezaki | |

(Continued)

FOREIGN PATENT DOCUMENTS

| | | |
|---|---|---|
| DE | 102007011329 A1 | 9/2008 |
| DE | 102008005265 A1 | 7/2009 |

(Continued)

*Primary Examiner* — Jyoti Nagpaul
(74) *Attorney, Agent, or Firm* — Sughrue Mion, PLLC

(57) ABSTRACT

A method for treating a tissue sample including placing at least one tissue sample on an cassette which has: a retaining member, a base and at least one biasing element; placing the at least one tissue sample in the tissue cassette; attaching the base and the retaining member to retain the tissue sample; processing the tissue sample in the tissue cassette with one or more solvents; and embedding the tissue sample in a paraffin to form an portion of paraffin in which the tissue sample is embedded in the tissue cassette, wherein the embedding comprises adding molten paraffin to the interior area of the tissue cassette and allowing the paraffin to become solid.

17 Claims, 8 Drawing Sheets

(56) References Cited

U.S. PATENT DOCUMENTS

| | | |
|---|---|---|
| 6,042,874 A | 3/2000 | Visinoni et al. |
| 6,103,518 A | 8/2000 | Leighton |
| 6,207,408 B1 | 3/2001 | Essenfeld et al. |
| 6,311,945 B1 | 11/2001 | D'Angelo |
| 6,329,645 B2 | 12/2001 | Giberson et al. |
| 6,372,512 B1 | 4/2002 | Kerschmann |
| 6,383,801 B1 | 5/2002 | Leighton |
| 6,444,170 B1 | 9/2002 | Heid et al. |
| 6,465,245 B1 | 10/2002 | Walton et al. |
| 6,468,783 B1 | 10/2002 | Leighton |
| 6,513,803 B2 | 2/2003 | Morales et al. |
| 6,521,186 B1 | 2/2003 | Izvoztchikov et al. |
| 6,586,713 B2 | 7/2003 | Essenfeld et al. |
| 6,596,479 B1 | 7/2003 | Gray et al. |
| 6,793,890 B2 | 9/2004 | Morales et al. |
| 6,797,928 B2 | 9/2004 | Giberson et al. |
| 6,803,018 B1 | 10/2004 | Stiller |
| 6,875,583 B2 | 4/2005 | Giberson et al. |
| 6,902,928 B2 | 6/2005 | Izvoztchikov et al. |
| 6,991,934 B2 | 1/2006 | Walton et al. |
| 7,005,110 B2 | 2/2006 | Taft et al. |
| 7,075,045 B2 | 7/2006 | Visinoni |
| 7,155,050 B1 | 12/2006 | Sloge et al. |
| 7,156,814 B1 | 1/2007 | Williamson, IV et al. |
| 7,179,424 B2 | 2/2007 | Williamson, IV et al. |
| 7,217,392 B2 | 5/2007 | Bogen et al. |
| 7,219,884 B2 | 5/2007 | Morales |
| 7,273,587 B1 | 9/2007 | Birkner et al. |
| 7,273,720 B1 | 9/2007 | Birkner et al. |
| 7,329,533 B2 | 2/2008 | Fredenburgh |
| 7,470,401 B2 | 12/2008 | Morales |
| 7,521,021 B2 | 4/2009 | McCormick |
| 7,526,987 B2 | 5/2009 | Morales |
| 7,544,953 B2 | 6/2009 | Goodman |
| 7,547,538 B2 | 6/2009 | Morales et al. |
| 7,553,672 B2 | 6/2009 | Bogen et al. |
| 7,575,556 B2 | 8/2009 | Speeg et al. |
| 7,576,307 B2 | 8/2009 | Yazdanfar et al. |
| 7,584,019 B2 | 9/2009 | Feingold et al. |
| 7,593,787 B2 | 9/2009 | Feingold et al. |
| 7,603,201 B2 | 10/2009 | Feingold et al. |
| 7,618,828 B2 | 11/2009 | Bleuel et al. |
| 7,657,070 B2 | 2/2010 | Lefebvre |
| 7,663,101 B2 | 2/2010 | Goodman |
| 7,666,620 B2 | 2/2010 | Wiederhold |
| 7,687,255 B2 | 3/2010 | Chu |
| 7,722,810 B2 | 5/2010 | Allen et al. |
| 7,767,434 B2 | 8/2010 | Chu |
| 7,776,274 B2 | 8/2010 | Williamson, IV et al. |
| 7,780,919 B2 | 8/2010 | McCormick |
| 7,850,912 B2 | 12/2010 | Favuzzi et al. |
| 7,881,517 B2 | 2/2011 | Sloge et al. |
| 7,888,132 B2 | 2/2011 | McCormick |
| 7,901,634 B2 | 3/2011 | Testa et al. |
| 7,914,462 B2 | 3/2011 | Hutchins et al. |
| 7,914,738 B2 | 3/2011 | Hutchins et al. |
| 2005/0084425 A1 | 4/2005 | Williamson, IV et al. |
| 2005/0112032 A1 | 5/2005 | McCormick |
| 2005/0142631 A1 | 6/2005 | Mosconi et al. |
| 2005/0147538 A1 | 7/2005 | Williamson, IV et al. |
| 2006/0147896 A1 | 7/2006 | Schnetz et al. |
| 2006/0177812 A1 | 8/2006 | Schnetz et al. |
| 2006/0228772 A1 | 10/2006 | Donndelinger |
| 2007/0072167 A1 | 3/2007 | Rochaix |
| 2007/0104618 A1 | 5/2007 | Williamson, IV et al. |
| 2007/0116612 A1 | 5/2007 | Williamson, IV |
| 2007/0141711 A1 | 6/2007 | Stephens et al. |
| 2007/0161609 A1 | 7/2007 | Buck et al. |
| 2007/0166834 A1 | 7/2007 | Williamson, IV et al. |
| 2007/0218542 A1 | 9/2007 | Li et al. |
| 2008/0026366 A1 | 1/2008 | Harkins |
| 2008/0138854 A1 | 6/2008 | Williamson |
| 2008/0193014 A1 | 8/2008 | Ecker et al. |
| 2008/0206807 A1 | 8/2008 | Duymelinck et al. |
| 2008/0220468 A1 | 9/2008 | Windeyer et al. |
| 2008/0227144 A1 | 9/2008 | Nightingale |
| 2008/0254504 A1 | 10/2008 | Vom et al. |
| 2008/0268496 A1 | 10/2008 | Mosconi et al. |
| 2008/0274496 A1 | 11/2008 | Duymelinck et al. |
| 2009/0098522 A1 | 4/2009 | Marcovitz |
| 2009/0145920 A1 | 6/2009 | Kerrod et al. |
| 2009/0165940 A1 | 7/2009 | Baur et al. |
| 2009/0170152 A1 | 7/2009 | Reeser et al. |
| 2009/0191544 A1 | 7/2009 | DeLa Torre Bueno |
| 2009/0203066 A1 | 8/2009 | Perrut et al. |
| 2009/0208105 A1 | 8/2009 | Bystrov et al. |
| 2009/0222746 A1 | 9/2009 | Chirica et al. |
| 2009/0253199 A1 | 10/2009 | McCormick |
| 2010/0017030 A1 | 1/2010 | Feingold et al. |
| 2010/0055663 A1 | 3/2010 | Konrad et al. |
| 2010/0061632 A1 | 3/2010 | Young et al. |
| 2010/0075410 A1 | 3/2010 | Desai et al. |
| 2010/0092064 A1 | 4/2010 | Li |
| 2010/0093023 A1 | 4/2010 | Gustafsson et al. |
| 2010/0099140 A1 | 4/2010 | Donndelinger |
| 2010/0112624 A1 | 5/2010 | Metzner et al. |
| 2010/0112625 A1 | 5/2010 | Erben et al. |
| 2010/0144002 A1 | 6/2010 | Donndelinger |
| 2010/0167334 A1 | 7/2010 | Williamson, IV |
| 2010/0167338 A1 | 7/2010 | Amano et al. |
| 2010/0182877 A1 | 7/2010 | Chu |
| 2010/0184127 A1 | 7/2010 | Williamson, IV et al. |
| 2010/0208955 A1 | 8/2010 | Mehes et al. |
| 2010/0223935 A1 | 9/2010 | Donndelinger |
| 2010/0248301 A1 | 9/2010 | Ulbrich et al. |
| 2010/0278627 A1 | 11/2010 | Williamson, IV et al. |
| 2010/0279341 A1 | 11/2010 | Steiner et al. |
| 2010/0323395 A1 | 12/2010 | Ulbrich et al. |
| 2010/0330660 A1 | 12/2010 | Hutchins et al. |
| 2011/0008884 A1 | 1/2011 | Morales |
| 2011/0034341 A1 | 2/2011 | Mehes et al. |
| 2011/0045565 A1 | 2/2011 | Sanders et al. |
| 2011/0054679 A1 | 3/2011 | Lefebvre et al. |
| 2011/0060766 A1 | 3/2011 | Ehlke et al. |
| 2011/0076753 A1 | 3/2011 | Goerner et al. |

FOREIGN PATENT DOCUMENTS

| | | |
|---|---|---|
| DE | 102009010667 A1 | 9/2010 |
| EP | 0807807 A1 | 11/1997 |
| EP | 1508026 A0 | 2/2005 |
| EP | 1545775 A0 | 6/2005 |
| EP | 1682272 A0 | 7/2006 |
| EP | 1782737 A1 | 5/2007 |
| EP | 1975595 A1 | 10/2008 |
| EP | 1985383 A1 | 10/2008 |
| EP | 2002894 A1 | 12/2008 |
| EP | 2091440 A0 | 8/2009 |
| WO | 2004/028693 A1 | 4/2004 |
| WO | 2005/037182 A2 | 4/2005 |
| WO | 2008/073387 A1 | 6/2008 |
| WO | 2010/030358 A1 | 3/2010 |
| WO | 2010/085626 A1 | 7/2010 |
| WO | 2010/112316 A1 | 10/2010 |
| WO | 2011041495 A1 | 4/2011 |

* cited by examiner

METHOD FOR PROCESSING AND EMBEDDING TISSUE

BACKGROUND OF THE INVENTION

The present disclosure relates generally to the method and process of embedding a tissue sample in a tissue cassette.

A biopsy is the removal of a tissue sample to examine tissue for signs of cancer or other disorders. Tissue samples are obtained in a variety of ways using various medical procedures involving a variety of the tissue sample collection devices. For example, biopsies may be open (surgically removing tissue) or percutaneous (e.g. by fine needle aspiration, core needle biopsy or vacuum assisted biopsy).

After the tissue sample is collected, the tissue sample is analyzed at a lab (e.g. a pathology lab, biomedical lab, etc.) that is set up to perform the appropriate tests (such as histological analysis). Although this disclosure refers to a sample, it should be understood that the term sample can refer to one or more samples.

In order to properly process the tissue sample a series of steps may be performed including:
Grossing of the tissue sample by cutting the tissue sample to the proper size for analysis;
Fixing of the tissue sample to immobilize molecular components and/or prevent degradation;
Embedding the tissue sample in an embedding material, such as paraffin wax; and In conventional methods, the grossing step involves a lab technician cutting the tissue to the appropriate size for analysis and then placing the tissue in a tissue cassette. During the fixation stage, the cassettes may be exposed to a fixing agent or chemical (e.g., a solution of formaldehyde in water such as formalin) shortly after sample collection. For example, U.S. Pat. No. 7,156,814 discloses a cassette which can withstand tissue preparation procedures.

After the tissue sample has been processed, the medical professional, in conventional methods, removes the tissue sample from the individual cassette to perform the embedding step. Specifically, the medical professional carefully orients the tissue sample, based on, for example, the tissue type or cross-section required, into a mold containing an embedding material such as paraffin wax. Once the tissue is oriented properly in the mold, the molten material is cooled to fully embed the tissue sample and hold it in the proper orientation. The paraffin is used to hold the tissue sample in position while also providing a uniform consistency to further facilitate sectioning. While the term paraffin is used, this term is not limiting and describes an example of an embedding medium.

Then the tissue sample is removed and sliced into a plurality of thin sections (e.g., 2 to 25µ thick sections), often using a microtome, for further processing and inspection. Such sectioning of the tissue sample, and further processing such as staining, often helps a medical professional properly assess the tissue sample under a microscope (e.g. diagnose relationships between cells and other constituents of the tissue sample, or perform other assessments).

The current process requires human intervention at the grossing, embedding and loading steps. Such manual handling of the tissue sample can increase the likelihood of mis-identifying the tissue sample, cross contaminating the tissue samples, or losing part or the entire sample. Additionally, the numerous steps of manual manipulation can often increase the time that it takes to provide a proper assessment for each sample, once the tissue sample is collected.

SUMMARY OF THE INVENTION

This invention provides a method for treating a tissue sample in which the tissue sample may be orientated during the grossing step and remain in the same orientation during the subsequent embedding step. Through the multiple embodiments, the method of processing, fixing, and embedding the tissue sample in a tissue cassette of this invention reduces the manual handling of the tissue samples. Example embodiments of this application may address one or more of the above identified issues. However, an embodiment of this application need not solve, address, or otherwise improve on existing technologies.

DETAILED DESCRIPTION OF THE INVENTION

In the following detailed description, reference will be made to the accompanying drawing(s), in which similar elements are designated with similar numerals. The aforementioned accompanying drawings show by way of illustration and not by way of limitation, specific example embodiments and implementations consistent with principles of an example embodiment. These implementations are described in sufficient detail to enable those skilled in the art to practice an example embodiment and it is to be understood that other implementations may be utilized and that structural changes and/or substitutions of various elements may be made without departing from the scope and spirit of an example embodiment. The following detailed description is, therefore, not to be construed in a limited sense.

An example of a method for processing, embedding, and preparing a tissue sample 2 for analysis after extraction will now be described according to a non-limiting embodiment.

Figure 1D:
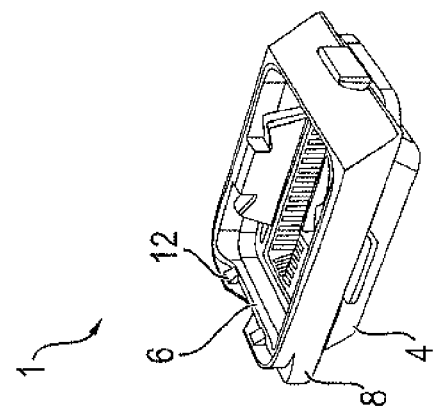
FIGS. 1A-1D illustrate a method of assembling a tissue cassette and placing a tissue sample in a tissue cassette according to a first embodiment.
Figure 1C:
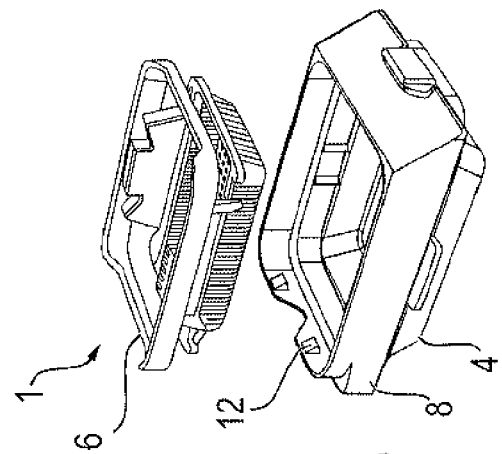
Figure 1B:
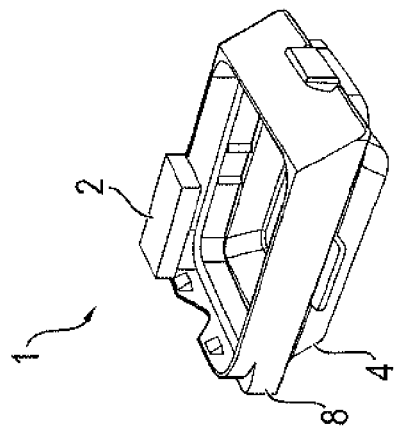
Figure 1A:
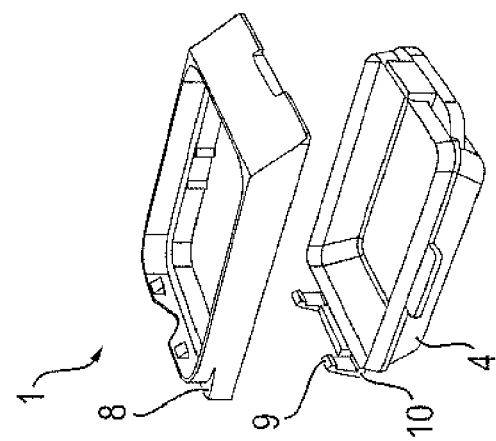

A tissue cassette 1 used to implement the method of the present invention is illustrated in FIGS. 1A-1D and disclosed in U.S. Patent Application No. 61/798,728, titled "Tissue Cassette with Biasing Element," which is incorporated herein by reference. As shown in FIG. 1A, the tissue cassette 1 has a base 4. In addition, a frame 8 may be optionally provided to surround the outer perimeter of the base 4. The base 4 may have a sealing member 10 which forms a liquid seal between the frame 8 and the base 4. As shown in FIG. 1B, according to a non-limiting embodiment, the tissue sample 2 may be placed in the tissue cassette 1. FIG. 1C illustrates the tissue cassette 1 further including a retaining member 6 provided to fit inside the base 4 and the frame 8. In this way, the retaining member 6 fits into the inside perimeter of the frame 8 and locks into place with the locking member 12 as shown in FIG. 1D. When the tissue cassette is assembled and attached, the base 4 and the retaining member 6 cooperate to retain the tissue sample 2, as discussed below. Accordingly, the tissue sample 2 may rest on either the base 4 or the retaining member 6 when the tissue sample 2 is placed in the tissue cassette 1.

Figure 2:
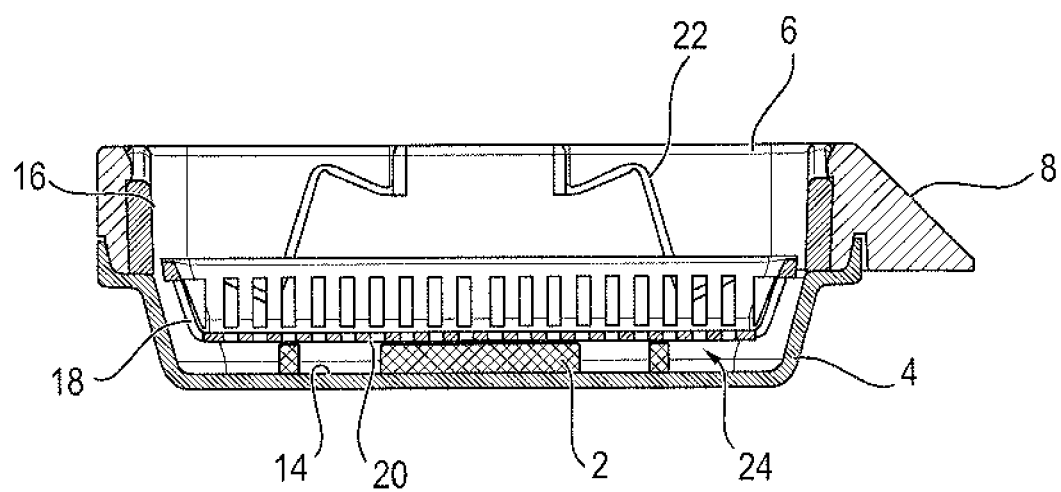
FIG. 2 shows an interior sectional view of the tissue cassette in an assembled state.

FIG. 2 shows a close-up view of a tissue cassette 1 according to a non-limiting embodiment. In this embodiment, the retaining member 6 is formed with a rim portion 16 and a tissue retaining element 18 having a bottom surface corresponding to a first tissue engaging surface 20. The base 4 has a bottom surface which corresponds to a second tissue engaging surface 14. Further, in a non-limiting embodiment, the retaining member 6 includes a biasing element 22.

Generally, when the base 4 and the retaining member 6 are engaged as shown in FIG. 2, an interior area 24 is defined between the base 4 and the retaining member 6 where the first tissue engaging surface 20 and the second tissue engaging surface 14 are facing each other. Prior to this engagement, a tissue sample 2 is placed into the interior area 24 in the desired orientation so that it rests on either the first tissue engaging surface 20 of the retaining member 6 or the second tissue engaging surface 14 of the base 4. Upon engagement of the retaining member 6 to the base 4, the biasing element 22 urges the first tissue engaging surface 20 of the tissue retaining element 18 towards the second tissue engaging surface 14 of the base 4 to firmly hold the tissue sample 2 in the chosen orientation between the first and second tissue engaging surfaces 14, 20 such that it can later be processed and embedded in the tissue cassette 1.

In a non-limiting embodiment, the first tissue engaging surface 20 may have protrusions 46 to stop moving towards the second tissue engaging surface once it contacts the tissue sample 2. As an additional precaution, as shown in FIG. 2, the tissue retaining element 18 may also have protrusions 46 which extend downwardly from the tissue retaining element 18 towards the base 4. The protrusions 46 which act as dead stops to prevent the tissue retaining element 18 from extending too far and pushing down too hard against the tissue sample 2 or potentially damaging the tissue sample 2.

Figures 3A, 3B:
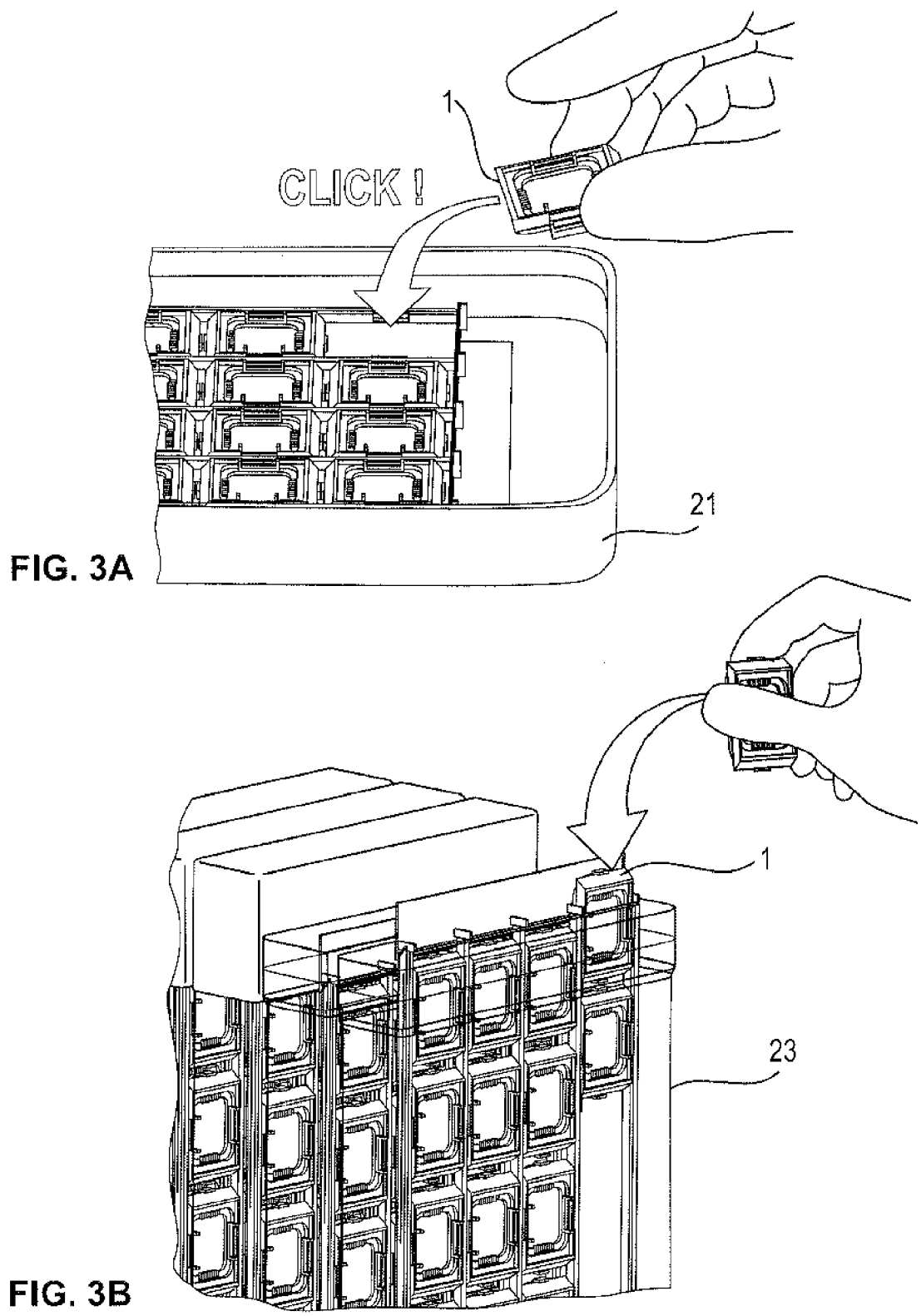
FIGS. 3A-3B illustrates loading cassettes onto a carrier which is subsequently immersed in fixative.

The steps of processing the tissue sample 2 with one or more solvents are shown in FIGS. 3A-B. Once the tissue sample 2 is properly placed in the tissue cassette 1, the tissue cassette 1 may be processed with one or more solvents as shown in FIG. 3A. Specifically, in a non-limiting embodiment, the tissue cassette may be placed in a processing carrier 21 which can hold one or more tissue cassettes 1 and may contain a solvent for processing the tissue sample. As shown in FIG. 3B, after the tissue is placed in the processing carrier 21, the processing carrier 21 may be placed into a container 23 holding a solvent, such as formalin, for additional processing of the tissue sample.

Figure 4A:
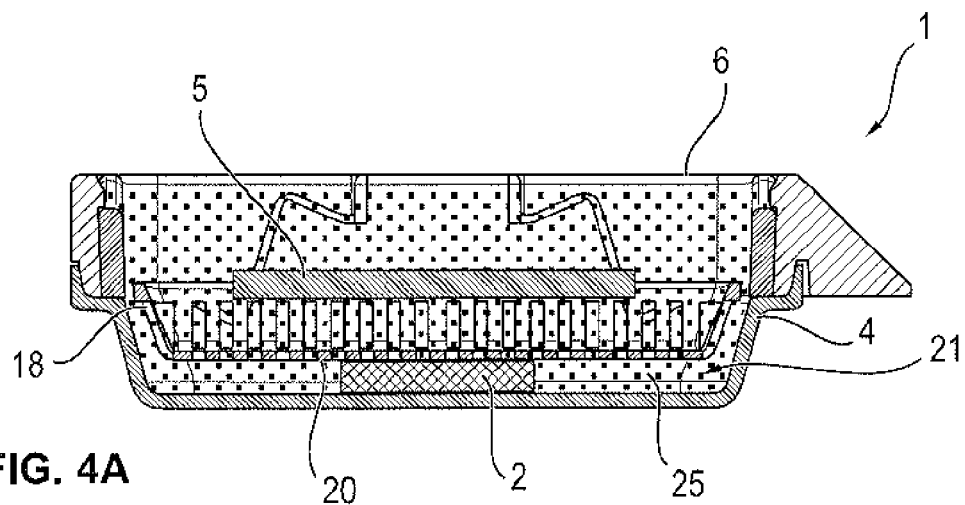
FIGS. 4A-4C illustrate a method of embedding a tissue sample according to a first embodiment.
Figure 4B:
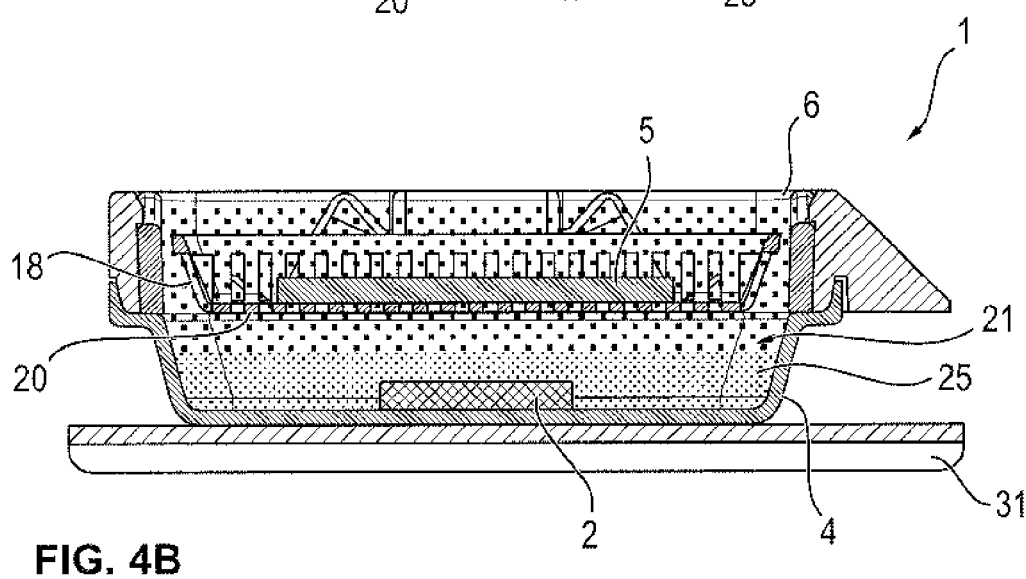
Figure 4C:
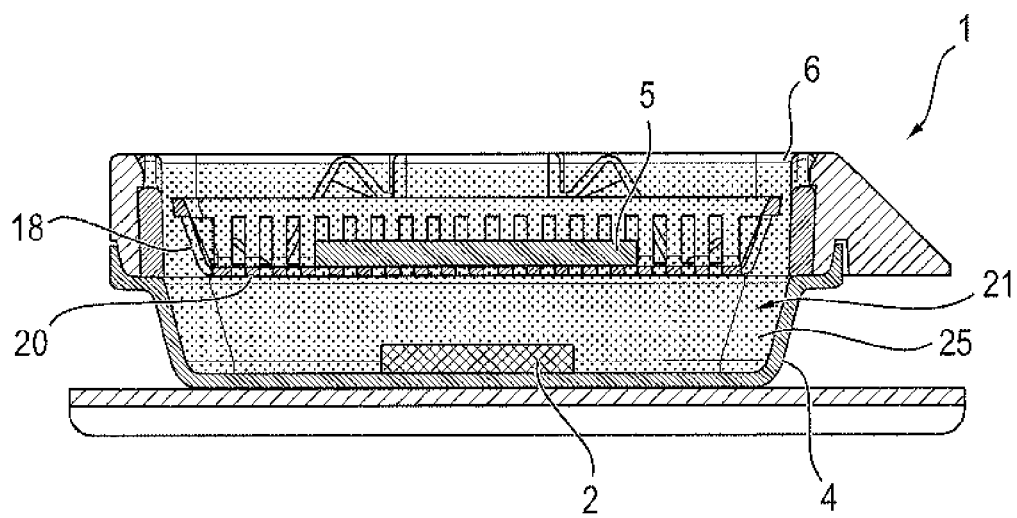

The step of embedding the tissue sample 2 will now be described with respect to FIGS. 4A-4C. As shown in FIG. 4A, paraffin 25 is added to the tissue cassette 1 to embed the tissue sample 2. The molten paraffin infiltrates the tissue cassette 1 and enters the interior area 24 and up to the top of the volume enclosed by walls of the frame 8 to embed the tissue sample 2 in its oriented position. As shown in FIG. 4B, after paraffin 25 has been added to the tissue cassette 1, the tissue cassette 1 is held against a cooling plate 31 such that the paraffin 25 at the bottom of the tissue cassette 1 starts to cool. When the paraffin starts to cool, a first, thin layer of solidified paraffin 25 adheres the tissue sample 2 to the base 4 to partially secure the tissue sample 2 to the base 4. While the paraffin 25 is still molten in the upper region of the tissue cassette, a retracting member 5 connected to the retaining member 6 pulls the first tissue engaging surface 20 of the retaining element 18 upwardly away from the tissue sample 2 and through the molten paraffin layers 25. The first tissue engaging surface 20 is held in a position away from the tissue sample 2 until the remaining paraffin 25 has solidified as shown in FIG. 4C. In this manner, the paraffin completely covers the upper surface of the tissue sample 2.

As shown in FIGS. 4A-4C and explained above, the retracting member 5 is disposed on the retaining member 6 for retracting the biasing element 18 and retracting the retaining element 18 from the tissue sample 2. The retracting member 5 can take on any form or shape that serves this function. For example, the retracting member 5 may comprise of a ferromagnetic member that can be moved by magnetic attraction, a mechanical member, such as a level, tab or contact point, or shaped memory polymer. Details of the retracting member are provided in U.S. Patent Application No. 61/799,441, titled "Tissue Cassette with Retractable Member" which is incorporated herein by reference.

Once the paraffin 25 has solidified and the tissue sample 2 is embedded, the base 4 may be detached from the retaining member 6 to expose one end of the embedded tissue sample while still remaining attached to either the first tissue engaging surface 20 or the second tissue engaging surface 14.

Figure 5:
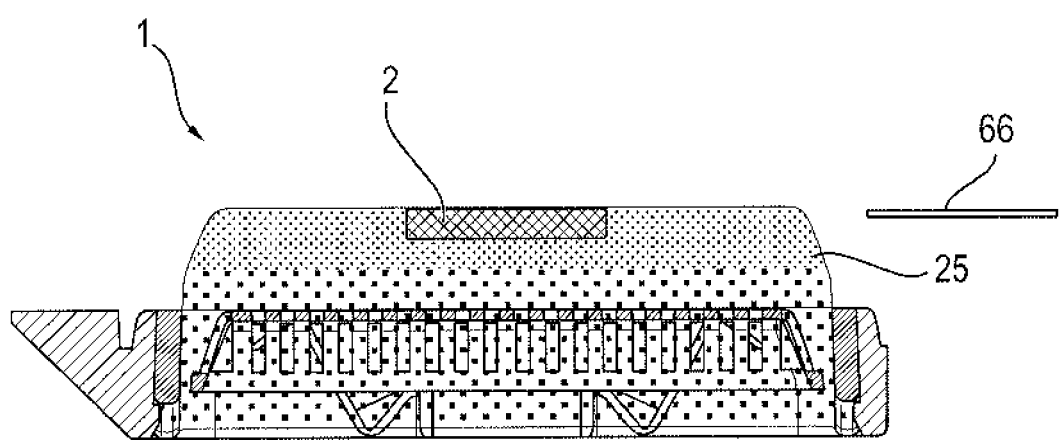
FIG. 5 is a side view of the tissue cassette according to an alternative embodiment.

As shown in FIG. 5, a cutting element 66 may be used to slice a layer of the embedded tissue to create a tissue section. In a non-limiting embodiment, the embedded tissue sample 2 may be sectioned using a microtone. After the tissue sample 2 is sliced it is ready to be placed on a substrate, for example a microscope slide, for further processing and inspection.

Figure 6:
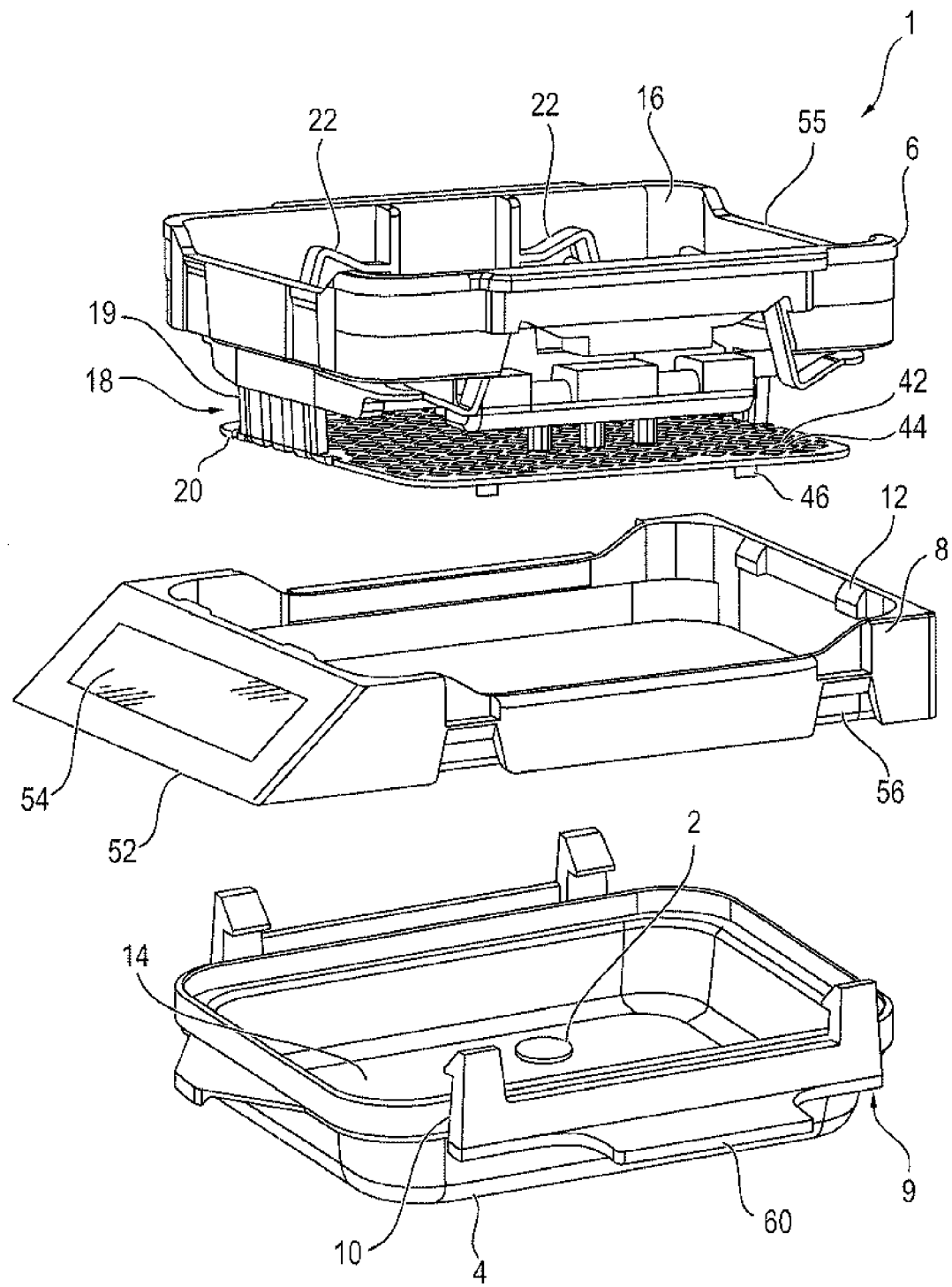
FIG. 6 is an exploded view of a tissue cassette according to a first embodiment in a non-assembled state.

The individual components of the tissue cassette will now be described in more detail with respect to FIG. 6. FIG. 6 shows an exploded view of the tissue cassette 1 according to a non-limiting embodiment. In this exemplary embodiment, the retaining member 6 has a rim 16, a biasing member 22 which connects the rim 16 to the retaining element 18, and a first tissue engaging surface 20 on the retaining element 18. In a non-limiting embodiment, the tissue retaining element 18 is attached to the rim portion 16 by the biasing element 22. The first tissue engaging surface 20 of the tissue retaining element 18 may also be attached directly to the biasing element 22. Alternatively, the first tissue engaging surface 20 of the tissue retaining element 18 may be connected to the biasing element 22 by a connecting portion 19, which as shown in FIG. 6, may extend from the first tissue engaging surface 20 towards the rim portion 16. The connector 19 connects the first tissue engaging surface 20 to the biasing element 22.

The rim 16 is provided with four walls and a substantially rectangular shape. On the inside of the rim 16 one end of the biasing member 22 is attached. The other end of the biasing member 22 attaches to the retaining element 18 at either a connector 19 or the first tissue engaging surface 20.

As shown in FIG. 6, the first tissue engaging surface 20 is provided with a substantially planar mesh portion 42. In this embodiment the mesh portion 42 is rectangular in shape, but the shape is not limiting and the mesh portion 42 can be a variety of shapes. The mesh portion 42 of the first tissue engaging surface 20 has a plurality of perforations 44 or cut-outs. When the mesh portion 42 is urged against the tissue sample 2 it holds the tissue sample 2 in place and allows reagents, or the like, to flow to the tissue sample 2 through the perforations 44 in the mesh portion 42. The perforations 44 are sized to allow the flow of fluid to the tissue sample 2 on the one hand, but to prevent the escape of the tissue sample 2 on the other hand. Thus, the perforations 44 in the mesh portion 42 may be sized according to the size of the tissue sample 2. Further, the first tissue engaging surface 20, may alternatively be solid and have no holes on the surface while still allowing the agent to flow underneath the first tissue engaging surface 20 from the periphery.

The base 4 will now be described with reference to FIG. 6. As discussed above, the tissue cassette 1 has a base 4 which supports the tissue sample 2 and holds the paraffin for embedding. The base 4 has a rectangular shape with four side walls and a depressed bottom planar surface, referred to as the second tissue engaging surface 14. The base 4 is not limited to this shape and a different shape could be used without changing the scope of the invention. The base 4 is preferably solid so that it can hold the paraffin for embedding. The walls of the base 4 are preferably tapered, for example inward, to improve the ease at which the base can be removed from the paraffin after the embedding process.

Figure 7:
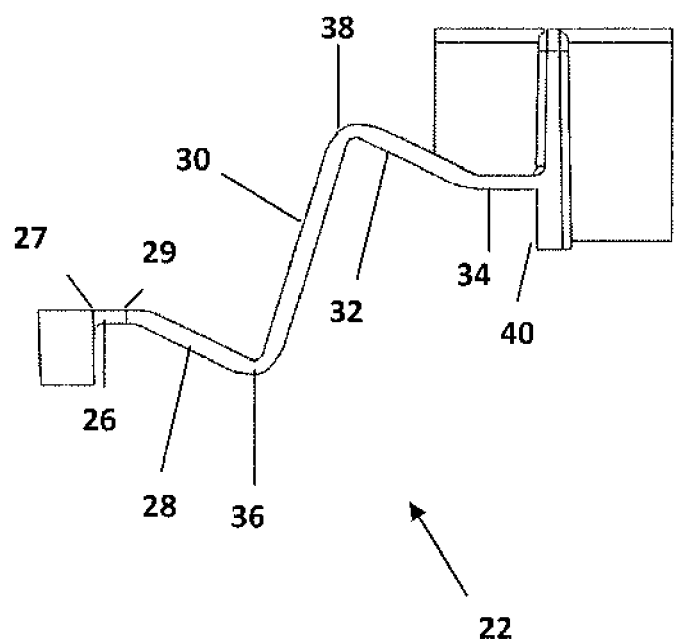
FIG. 7 shows a cut-out section of the biasing element on the tissue cassette of the above embodiment.

An example of a biasing element that may be used in the above described embodiment is shown in FIG. 7. As noted above the tissue retaining element 18 is attached to the retaining member 6 by at least one biasing element 22. In the illustrated embodiment in FIG. 1, the tissue cassette 1 has four biasing elements 22, where two biasing elements are shown in the Figure and the other two are on the opposite wall.

As shown in FIGS. 6 and 7, each biasing element 22 may have a substantially S or Z shape and attach at one end to the tissue retaining element 18 and attach at the other end to the inner surface of the rim portion 16. The biasing element 22 urges the tissue retaining element 18 towards the base 4 to fix the tissue sample 2 between the first and second tissue engaging surfaces 14, 20. Thus, the biasing element 22 can take on any shape that performs this function. For example, a torsion bar or a biasing element having another shape could also be used as discussed in more detail below.

More specifically, as shown in FIG. 7, each biasing element 22 has a first member 26 with a first end 27 and a second end 29. The first end 27 is connected to the tissue retaining element 18. Extending downward at an angle from the hinge or second end 29 of the first member 26 is a first angled member 28. A second angled member 30 is connected to the first angled member 28 by a first curved hinged point 36. The second angled member 30 extends upwardly from the first angled member 28 at an angle; and in a non-limiting embodiment, the second angled member 30 and the first angled member 28 form an angle less than 90°. Extending downwardly from the second angled member 30 is a third angled member 32. The second angled member 30 and the third angled member 32 are connected by a second curved hinge point 38. In a non-limiting embodiment, the third angled member 32 and the second angled member 30 form an angle less than 90°. Further, in a non-limiting embodiment, the third angled member 32 and the first angled member 28 form an angle less than 90°. A second member 34 connects to the third angled member 32 at a hinge point and extends substantially parallel to the tissue retaining element 18. The second member 34 attaches to the rim portion 16 of the retaining member 6 in a non-limiting embodiment. Additionally, a dead stop 40 may be provided adjacent to the second member 34 which prevents the first tissue engaging surface 20 from retracting passed its perimeter.

The biasing element 22 has a particular flexibility to ensure that the tissue sample 2 is held between the first and second tissue engaging surfaces 14, 20, on the one hand, but to also ensure that the tissue sample 2 withstands any permanent damage during processing.

As noted above, in some embodiments a frame 8 is placed around the outside perimeter of the retaining member 6 and functions to secure the retaining member 6 to the base 4. The frame 8 may also be used as a means for identifying the tissue sample. As shown in in FIG. 6, the frame 8 has a substantially rectangular shape with one end have an angled projection with an angled face 52. A label 54 may be placed on the angled face 52 to identify the tissue sample 2. The labels 54 are described in more detail below. In this embodiment, the angle of the planar face is about 45 degrees, but the invention is not limited in this respect. The angled face 52 can be configured to receive a label such that the label 54 clicks into the angled face 52 of the frame 8. Alternatively, the frame 8 may have a textured surface and be put through an inkjet printing system, such as Leica IPC ink jet printer. In this instance, the tissue cassette 1 can be assembled after printing or the base 4 along with the frame 8 can be configured to be sent through the printer.

In a non-limiting embodiment, the frame 8 and the retaining member 6 are not easily removed so that once the tissue cassette 1 is used, the label 54 on the frame 8 will remain matched with the tissue sample 2 contained in the tissue cassette 1. In certain embodiments, frame 8 has a locking projections 12 which projects from the inside the perimeter of the frame 8, shown in FIG. 6. The locking projections 12 attach with an engaging portions 55 on the outer perimeter of the rim portion 16 on the retaining member 6 to secure the frame 8 to the retaining member 6. Once the frame 8 is connected to the base 4 using this locking arrangement, it is difficult to separate them.

The base 4 includes a latching member 9 which acts as a clip or lock to hold the base 4 to the frame 8. Alternatively, if a frame 8 is not used, the latching member 9 can lock the base 4 to the retaining member 6.

As shown in FIG. 2, the latching member 9 is connected to a releasing member 60. The latching member 9 is flexibly attached to the base 4. When the latching member 9 is engaged, the latching member 9 attaches to the clip surfaces 56 on the outer perimeter of the frame 8. The latching member 9 locks the base 4 to the frame 8 which is attached to the retaining member 6. In this way, a sealing member 10 connects the latching member 9 to the base 4 to form a seal between the surfaces on the perimeter of the base 4 and the frame 8 to sufficiently prevent paraffin from leaking during embedding. In a non-limiting embodiment a gasket may be used as the sealing member 10 to help seal the base 4 and the frame 8. The latching member 9 is disengaged by pressing downward on the releasing member 60. When the releasing member 60 is pressed, the latching member 9 moves away from the base 4 and disengages from the clip surfaces 56. In the embodiment described above, the sealing member 10 extends from the base 4, but the sealing member 10 may also extend from the retaining member 6 or the frame 8. Without being limited by theory, the seal acts to assist retention of molten material during embedding.

An important aspect of tissue sample analysis is properly keeping track of tissue samples. In some embodiments, the tissue cassette 1 includes a label 54 or ID tag as shown in FIG. 6. The label can 54 be located anywhere on the tissue cassette 1, but is preferably located on the frame 8. In some embodiments, more than one tag may be present. When more than one tag is present, the tags can be physically separated or located together.

The label 54 may be a computer or human readable tag including, but not limited to, labels having an incorporated RFID, labels having an incorporated one-dimensional barcode (1-D barcode), labels having an incorporated two-dimensional barcode (2-D barcode), and labels having an incorporated three-dimensional barcode (3-D barcode). However, the computer readable label is not limited to RFID, 1-D barcode, 2-D barcode, or 3-D barcode labels and may include any type of label readable by a computer as would be apparent to a person of ordinary skill in the art.

In some embodiments, a label 54 is present that may be sensitive to changes to the tissue sample or itself. For example, a label 54 may be present that changes physical (i.e. color) or chemical (i.e. redox, conjugation, etc.) properties during fixation of the tissue sample. Similarly, a label 54 may be present that is sensitive to the processing steps which precede embedding (i.e. dehydration). Alternatively, a label 54 may be present that is sensitive to the embedding step (i.e. infiltration of paraffin). The label 54 may have a property that changes incrementally or switches when the step is complete. In this way, the technician, or an automated system, will be able to determine when the tissue sample has finished one step before another is started.

Figure 8:
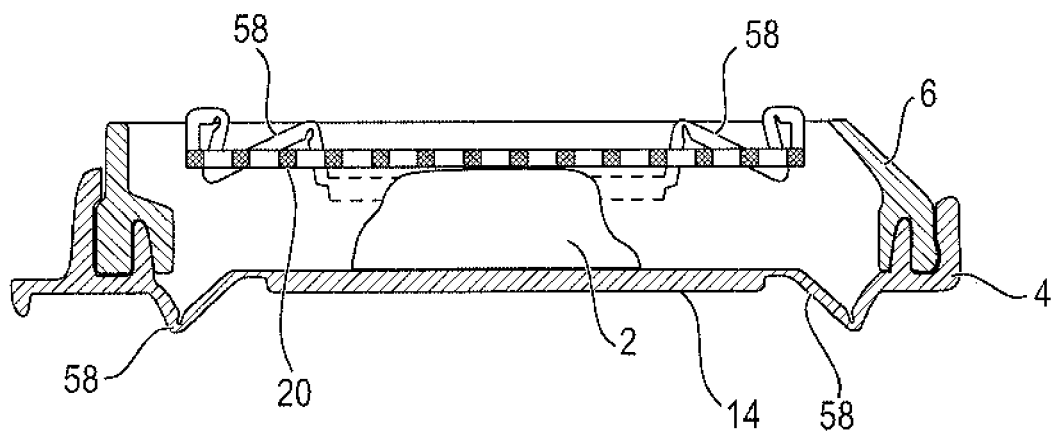
FIG. 8 is an interior side view of a tissue cassette according to another embodiment in an assembled state.

FIG. 8 shows a further embodiment of the tissue cassette 1. This embodiment is different from the previously described embodiments in that in this embodiment, a biasing member 58 may be provided on either the base 4 or the retaining member 6 or both, along with the biasing element 22 as described in the above embodiments. In this embodiment, the biasing member 58 on the retaining member 6 may be pushing down and the biasing member 58 attached to the base 4 may provide a biasing force to move the second tissue engaging surface 14 away from the first tissue engaging surface 20. Further, the biasing member 58 attached to the retaining member 6 may permit the retaining member 6 to move away from the base 4 in response to the biasing force provided by the base 4. Similarly, the biasing member 58 attached to the base 4 may permit the base 4 to move away from the retaining member 6 in response to the biasing force provided by the retaining member 6. In this embodiment, the tissue sample container 1 is stable when either the biasing member 58 attached to the retaining member 6 or biasing member 58 attached to the base 4 is applying a biasing force, or when both are applying or not a biasing force.

For example, the biasing member 58 on the base 4 may be used only to enable the releasing of the force that is applied by the biasing member 58 on retaining member 6. As an example, in this embodiment, the tissue cassette 1 provides a two position floor. The first position is when the biasing member 58 on the base 4 compresses the second tissue engaging surface 14 upwardly such that the tissue engaging surface is compressed up towards the retaining member 6 to compress the tissue sample 2. The second position is when the force of the biasing member 58 on the base is released so that the second tissue engaging surface 14 is moves downwardly. In this way, the second tissue engaging surface 14 retracts away from the tissue 2, such that the floor of the base retracts, similar to the first tissue engaging surface 20 of the previous embodiments retracting towards and away from the tissue sample 2. Other than these differences noted, the embodiment shown in FIG. 8 has the same configuration and tracks the same structure as discussed above.

The tissue cassette 1 can be made from various materials and the same or different materials can be used for the retaining member 6, including the retaining element 18, the first tissue engaging surface 20, the mesh portion 42, and the base 4. Examples of materials used include: an acetal copolymer, Teflon, polypropylene, and stainless steel. In a non-limiting embodiment, the acetal copolymer is DELRIN 900. In a non-limiting embodiment, the base 4 is made out of a polypropylene material so that the base 4 does not attach to the paraffin after the tissue sample 2 is embedded.

In a non-limiting embodiment, the tissue cassette, including the base, the retaining member, and/or the frame, may be produced from a material lacking any dye or coloring. The lack of color may allow the technician to view the tissue sample in the tissue cassette and ensure that the tissue sample has remained in its desired orientation after embedding. In these embodiments, the tissue cassette, including the base, the retaining member, and/or the frame may be at least at least opaque or clear.

Although a few example embodiments have been shown and described, these example embodiments are provided to convey the subject matter described herein to people who are familiar with this field. It should be understood that the subject matter described herein may be embodied in various forms without being limited to the described example embodiments. The subject matter described herein can be practiced without those specifically defined or described matters or with other or different elements or matters not described. It will be appreciated by those familiar with this field that changes may be made in these example embodiments without departing from the subject matter described herein as defined in the appended claims and their equivalents. Further, any description of structural arrangement of components or relationship there between is merely for explanation purposes and should be used to limit an example embodiment.

Aspects related to the example embodiment have been set forth in part in the description above, and in part should be apparent from the description, or may be learned by practice of embodiments of the application. Aspects of the example embodiment may be realized and attained using the elements and combinations of various elements and aspects particularly pointed out in the foregoing detailed description and the appended claims.

It is to be understood that both the foregoing descriptions are an example and are explanatory only and are not intended to be limiting.

What is claimed is:

1. A method for treating a tissue sample, comprising providing a tissue retaining cassette, comprising:
   a retaining member having an first tissue engaging surface and at least one biasing element, the first tissue engaging surface being moveably attached to the retaining member by said biasing element, and
   a base comprising a second tissue engaging surface and configured to engage the retaining member to form an interior area with the first and second tissue engaging surfaces facing each other;
   placing the at least one tissue sample on one of the first tissue engaging surface and the second tissue engaging surface;
   attaching the base and the retaining member to cause the biasing element to urge first tissue engaging surface towards the second tissue engaging surface, such that the tissue sample is held between the tissue engaging surfaces;
   processing the tissue sample in the tissue cassette with one or more solvents; and
   embedding the tissue sample in paraffin while the tissue is in the tissue cassette.

2. The method according to claim 1, further comprising.
   detaching the base from the retaining member such that the portion of paraffin in which the tissue sample is embedded remains attached to one of the first tissue engaging surface and the second tissue engaging surface.

3. The method according to claim 1, wherein the material in which the tissue sample is embedded is a wax.

4. The method according to claim 1, wherein the step of embedding the tissue sample in the paraffin comprises:
   retracting one of the first tissue engaging surface and the second tissue engaging surface away from the tissue sample after a portion of the paraffin has solidified and allowing a remaining portion of the paraffin to solidify.

5. The method according to claim 4, further comprising placing the tissue cassette on a cooling plate during the embedding and retracting steps.

6. The method according to claim 1, further comprising, after detaching the base from the retaining member, slicing a layer of paraffin from the portion of paraffin in which the tissue sample is embedded to create a tissue section.

7. The method according to claim 6, further comprising placing the tissue section on a substrate.

8. The method according to claim 1, further comprising placing a frame around the base and attaching the frame to the retaining member.

9. The method according to claim 8, further comprising applying a label to at least one of the retaining member, the base and the frame.

10. The method according to claim 9, wherein the label comprises a computer readable ID tag.

11. The method according to claim 10, further comprising encoding the computer readable ID tag with information unique to the tissue sample.

12. The method according to claim 9, wherein the information unique to the tissue sample includes one or more of patient identification information, sample collection site location information, collection temperature, collection time, and collection conditions.

13. A method for treating a tissue sample, comprising providing a tissue cassette, comprising:
    a retaining member having an first tissue engaging surface and at least one biasing element, the first tissue engaging surface being moveably attached to the retaining member by said biasing element, and
    a base comprising a second tissue engaging surface and configured to engage the retaining member to form an interior area with the upper and second tissue engaging surfaces facing each other;
placing the at least one tissue sample on one of the first tissue engaging surface and the second tissue engaging surface;
attaching the base and the retaining member to cause the biasing element to urge first tissue engaging surface towards the second tissue engaging surface, such that the tissue sample is held between the tissue engaging surfaces; and
processing the tissue sample in the tissue cassette with one or more solvents.

14. The method according to claim 13, further comprising, embedding the tissue sample in a paraffin to form a portion of paraffin in which the tissue sample is embedded in the tissue cassette, wherein the embedding comprises adding molten paraffin to the interior area of the tissue cassette and allowing the paraffin to become solid.

15. A method for treating a tissue sample, comprising
placing at least one tissue sample on a cassette having a base and a retaining member,
processing the tissue sample in the tissue cassette with one or more solvents,
embedding the tissue sample in paraffin to form a portion of paraffin in which the tissue sample is embedded in the tissue cassette, and
slicing the tissue sample which is embedded in the paraffin into layers to create a tissue section,
wherein in the processing, embedding, and slicing steps are preformed while the tissue sample is attached to at least one of the base and the retaining member.

16. A method for treating a tissue sample, comprising providing a tissue cassette comprising:
    a retaining member having a first tissue engaging surface;
    a base having a second tissue engaging surface; and
    at least one biasing element,
        at least one of the first tissue engaging surface and the second tissue engaging surface is moveably attached to at least one of the retaining member and the base by said biasing element, and
        the base and the retaining member are configured to engage each other to form an interior area with the first and second tissue engaging surfaces facing each other,
attaching the base and the retaining member to cause the biasing element to urge first tissue engaging surface towards the second tissue engaging surface, such that the tissue sample is held between the tissue engaging surfaces; and
processing the tissue sample in the tissue cassette with one or more solvents.

17. The method according to claim 16, further comprising, embedding the tissue sample in a paraffin to form an portion of paraffin in which the tissue sample is embedded in the tissue cassette, wherein the embedding comprises adding molten paraffin to the interior area of the tissue cassette and allowing the paraffin to become solid.

* * * * *